United States Patent
Gomo et al.

(10) Patent No.: US 11,684,280 B2
(45) Date of Patent: Jun. 27, 2023

(54) PULSE METER FOR NEWBORN

(71) Applicant: Laerdal Medical AS, Stavanger (NO)

(72) Inventors: Øystein Gomo, Hundvåg (NO); Helge Myklebust, Stavanger (NO); Joar Eilevstjønn, Sandnes (NO)

(73) Assignee: LAERDAL MEDICAL AS, Stavanger (NO)

( * ) Notice: Subject to any disclaimer, the term of this patent is extended or adjusted under 35 U.S.C. 154(b) by 642 days.

(21) Appl. No.: 16/619,125

(22) PCT Filed: Jun. 7, 2018

(86) PCT No.: PCT/EP2018/065017
§ 371 (c)(1),
(2) Date: Dec. 4, 2019

(87) PCT Pub. No.: WO2018/224593
PCT Pub. Date: Dec. 13, 2018

(65) Prior Publication Data
US 2020/0113460 A1    Apr. 16, 2020

(30) Foreign Application Priority Data
Jun. 7, 2017   (NO) .................................... 20170925

(51) Int. Cl.
*A61B 5/024*      (2006.01)
*A61B 5/0245*     (2006.01)
*A61B 5/00*       (2006.01)

(52) U.S. Cl.
CPC ........ *A61B 5/02438* (2013.01); *A61B 5/0245* (2013.01); *A61B 5/6823* (2013.01); *A61B 2503/045* (2013.01)

(58) Field of Classification Search
CPC .......... A61B 2503/045; A61B 5/02438; A61B 5/0245; A61B 5/6823
(Continued)

(56) References Cited

U.S. PATENT DOCUMENTS 6,928,317 B2 * 8/2005 Chen .................... A61B 5/6831
600/509
2005/0177051 A1   8/2005 Almen
(Continued)

FOREIGN PATENT DOCUMENTS

EP    1199028 A2    4/2002
EP    2900128 A2 *  8/2015   ........... A61B 5/0004
(Continued)

OTHER PUBLICATIONS

Trattner, Barbara; International Search Report for PCT/EP2018/065017 dated Sep. 7, 2018; 5 pages.

*Primary Examiner* — Carl H Layno
*Assistant Examiner* — Michael J Lau
(74) *Attorney, Agent, or Firm* — Bradley Arant Boult Cummings LLP

(57) ABSTRACT

A bow shaped pulse meter for new-born patients, comprising a control unit arranged in a central portion of the pulse meter, a first arm with an integrated first electrode and a second arm with an integrated second electrode extending respectively in a bow from opposite sides of the central portion, the integrated electrodes are configured to be in contact with a patient body (not shown) when in use, the electrodes being further electrically connected to the control unit. The pulse meter being distinctive in that the first and second arm and the control unit comprising an integral core element being made of a material having flexible properties to allow the respective arms to bend away from each other when the pulse meter is being arranged into an applying or removing position on the patient's body, the material having further spring back properties so that the arms naturally contract inwards such that the electrodes are maintained in contact with the patient's body when the pulse meter is in the applied position, the pulse meter further comprising a second layer overmolding at least a portion of each arm of the
(Continued)

core element, the material of the second layer being electro conductive forming a connection between the electrodes and the control unit.

15 Claims, 5 Drawing Sheets

(58) Field of Classification Search
USPC .......................................................... 600/390
See application file for complete search history.

(56) References Cited

U.S. PATENT DOCUMENTS

| | | | | |
|---|---|---|---|---|
| 2013/0131484 | A1* | 5/2013 | Pernu ................... | A61B 5/0245 600/388 |
| 2014/0303472 | A1* | 10/2014 | Callahan ................ | A61B 5/274 600/394 |
| 2016/0120434 | A1* | 5/2016 | Park ....................... | G16H 50/30 600/301 |
| 2016/0165719 | A1* | 6/2016 | Li ........................... | H05K 3/30 361/749 |
| 2017/0000415 | A1* | 1/2017 | Lapetina ............ | A61B 5/02438 |
| 2017/0049352 | A1* | 2/2017 | Mirov ................ | A61B 5/6885 |

FOREIGN PATENT DOCUMENTS

| | | | | |
|---|---|---|---|---|
| EP | 2900128 B1 | * | 7/2016 | ........... A61B 5/0004 |
| WO | WO-2011131234 A1 | | 10/2011 | |
| WO | WO-2014048807 A2 | | 4/2014 | |

* cited by examiner

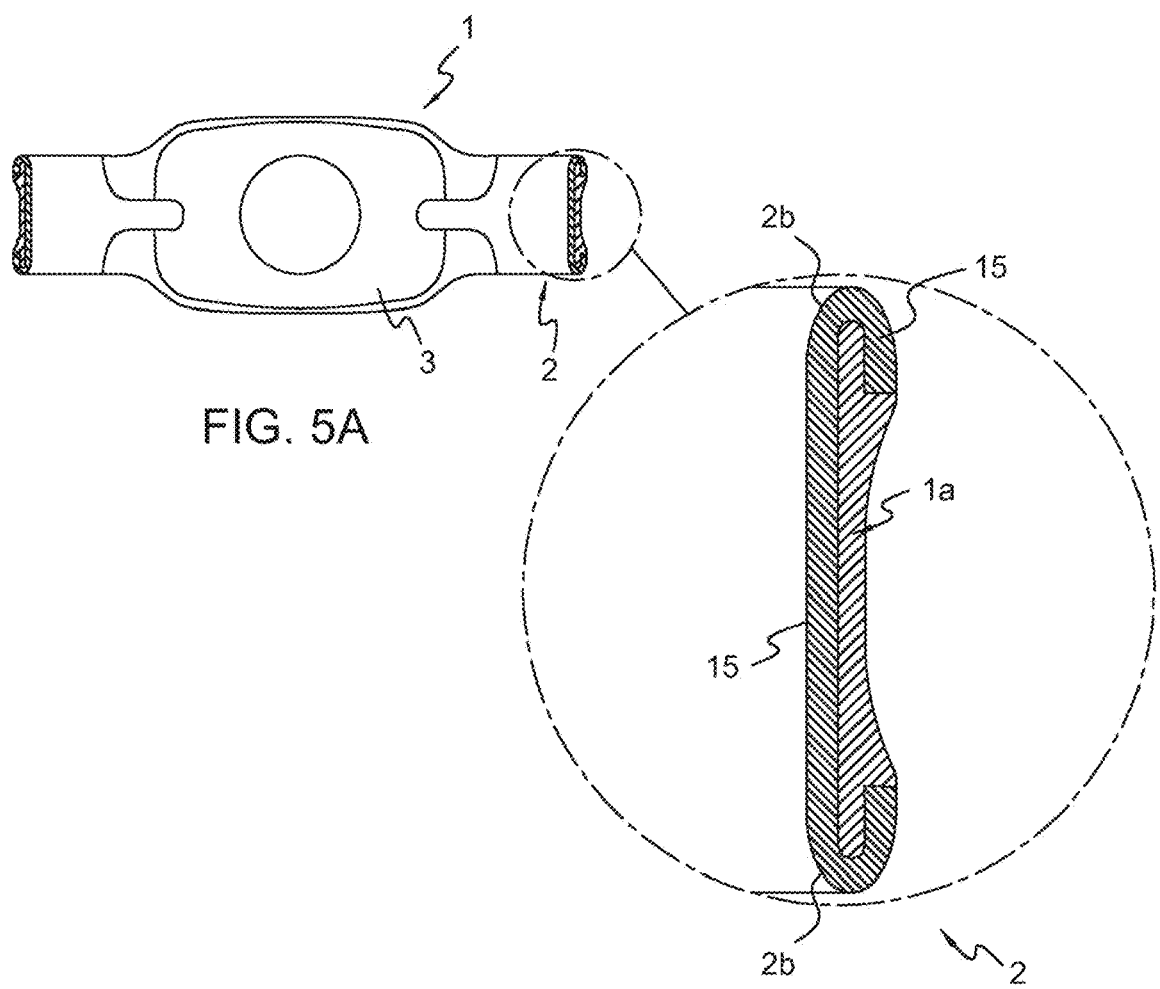
FIG. 5A
FIG. 5B
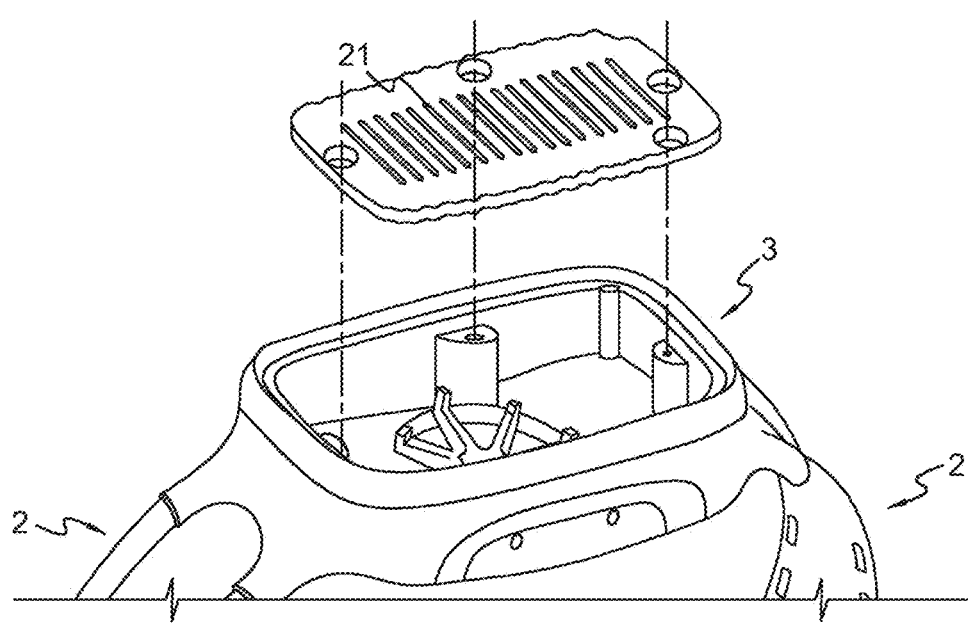
FIG. 6

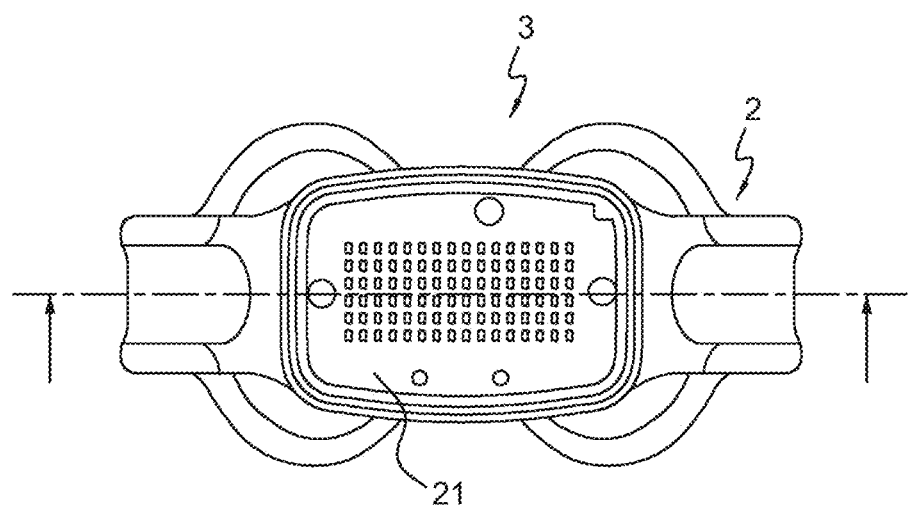
FIG. 7
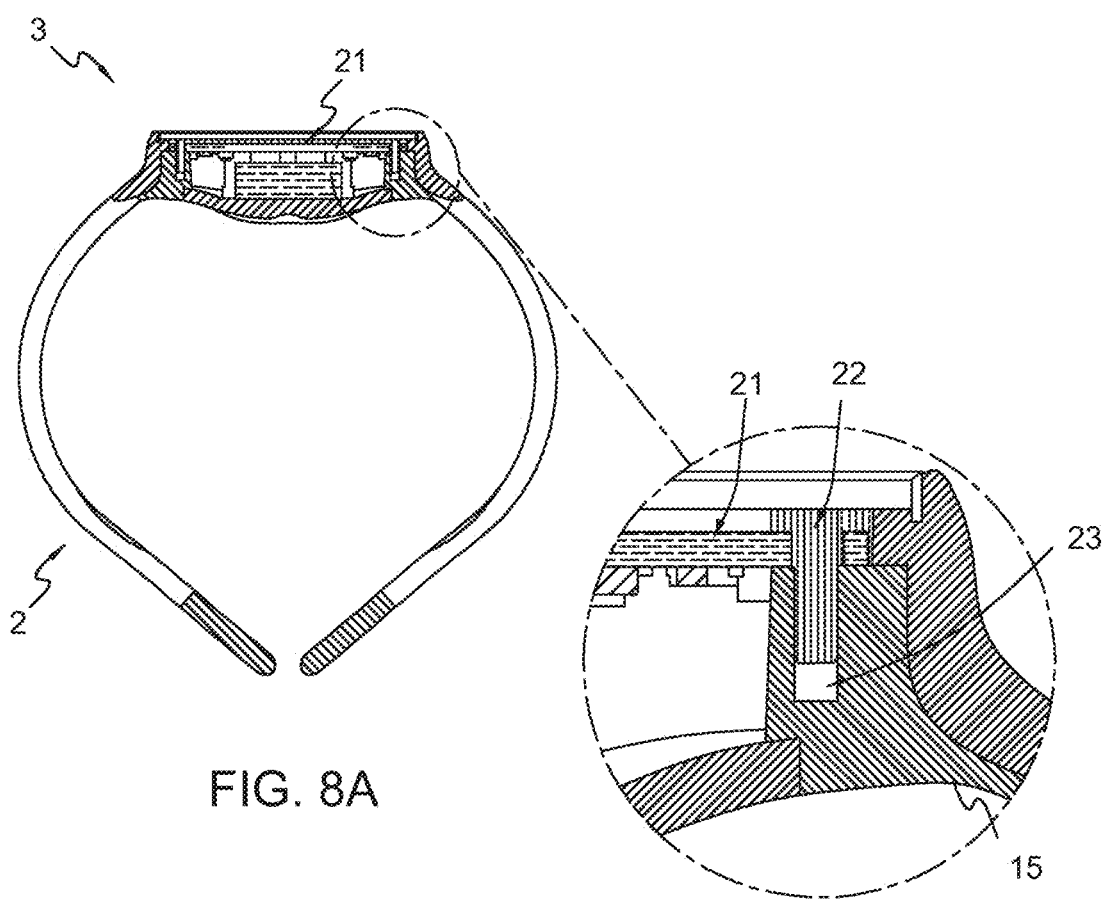
FIG. 8A
FIG. 8B

PULSE METER FOR NEWBORN

TECHNICAL FIELD

The present invention relates to a pulse meter for use on newborns of different sizes, in particular the invention relates to a bow shaped pulse meter that is fitted around the torso of the baby to provide heart rate information from a baby in a simple way.

BACKGROUND ART

Stillbirth and birth asphyxia is the cause of 10 million newborn resuscitations every year, of which 2 million dies. Proper diagnosis and prompt initiation of facemask ventilation can save many lives. Most resuscitations follow algorithms and these algorithms again use heart rate to guide therapy. Current methods to measure newborn heart rate are neither fast nor accurate, or appropriate for a midwife who works alone. Palpating the umbilical cord and auscultation with a stethoscope may be fast, but it is not accurate. Conventional ECG is accurate, but not sufficiently fast. Pulse oximetry (SpO2) is neither fast nor accurate.

Knowing that the risk of death increases by 16% for every 30 seconds delay to start facemask ventilation, initial heart rate assessment should not delay face mask ventilation. Once resuscitation has started, heart rate should guide facemask ventilation. When heart rate is low, ventilation is needed. Ventilation is effective when it causes heart rate to increase. The clinical importance of assessing heart rate for newborns is emphasized in the 2015 CPR guidelines.

WO2011131234 discloses a sensor apparatus to be incorporated in a garment. The apparatus discloses one or more sensors, which is comfortable to use and to which an electronic device may easily be connected. The sensor apparatus further discloses a first and second textile layer which is used on the inside and outside of the garment that makes the garment comfortable in use. The sensor apparatus further discloses a third intermediate layer that is substantially more rigid to provide more stiffness to the local area so that the electronic device may be easily attached to the garment. This intermediate layer is however not flexible or bendable.

Thus, the problem associated with the prior art is the need to provide a device that measure the pulse in newborn babies of different sizes in a fast, gentle, simple and reliable manner.

OBJECT OF THE INVENTION

It is an object of the invention to provide heart rate information in a gentle, simple, fast and reliable way to reduce the risk of death of newborn babies.

It is another object of the invention to provide a pulse meter that can accommodate newborn babies of different size so that the pulse meter stays snugly on the baby body to measure the heart rate information or other relevant information about the baby' health condition.

It is yet another object of the invention to provide a pulse meter that is smooth and easy to clean.

It is yet another object of the invention to provide a pulse meter that is soft and provides a gentle touch against the baby's body.

It is also another object of the invention to provide a pulse meter where the flexible arms are thin to provide a gentle holding force around the torso of the baby as well as keeping the pulse-meter light.

It is also an object of the invention to provide a nice and "child friendly" appearance of the pulse meter.

It is also an object of the invention to further increase the electrical signal quality to the pulse meter.

It is yet another object of the invention to display the heart rate at the location where the focus of the healthcare provider already should be; on the newborn itself, not on a remote monitor.

It is another object of the invention to use an electrically conductive, soft plastics to give a soft touch against the baby's body, while picking up the electrical signals from the baby's skin and conduct them to the electronic control unit. The combination of the soft, electrically conductive material and another material with good spring-properties gives a firm contact around the baby's body and ensures both the fixation of the device and the detection and conduction of the ECG-signals.

Metal electrodes could be embedded into the conductive to improve the signal quality.

SUMMARY OF INVENTION

The invention relates to a bow shaped pulse meter for new-born patients, comprising a control unit arranged in a central portion of the pulse meter, a first arm with an integrated first electrode and a second arm with an integrated second electrode extending respectively in a bow from opposite sides of said central portion, said integrated electrodes are configured to be in contact with a patient body (not shown) when in use, said electrodes being further electrically connected to said control unit.

The first and second arm and the control unit comprising an integral core element being made of a material having flexible properties to allow the respective arms to bend away from each other when the pulse meter is being arranged into an applying or removing position on the patient's body, said material having further spring back properties so that the arms naturally contract inwards such that said electrodes are maintained in contact with the patient's body when the pulse meter is in the applied position, said pulse meter further comprising a second layer overmolding at least a portion of each arm of core element, said material of the said second layer being electro conductive forming the electrical connection between the electrodes and the control unit.

The thin, flexible arms having spring back effect that gives sufficient press inward when expanded (flexible) to ensure proper electrical contact to the skin and can also adjust to different shapes of the torso of newborn babies. The arms are also flexible so that they may be bent outwards and inwards from a resting position. The combination of the soft, electrically conductive layer and the core material with combined flexible and spring back properties gives a firm and tight contact around the baby's body. This ensures both the fixation of the device and the detection and conduction of the ECG-signals.

The electrodes do also not require gel to function, but are so called dry electrodes.

The core element is further made of a material that is firm and highly flexible. The pulse meter is in the resting position configured to close around the baby's body.

In another embodiment of the invention, the core element consisting of a flexible material with good spring properties such as for example one of the material Polycarbonate (PC), ABS, Polyamide (PA), POM or spring steel.

In another preferred embodiment of the pulse-meter, the second layer consisting of a soft polymer material, such as carbon filled thermoplastic polyurethane, thermoplastic urethane (TPU), thermoplastic elastomer (TPE) rubber, silicone or polyvinylchloride (PVC) having an electrically conductive additive.

In a further preferred embodiment, the material of the second layer is made of a flexible material.

In another preferred embodiment of the pulse-meter, the second layer is overmolding the edges extending along the longitudinal side of each of the respective arms.

In yet another embodiment of the invention, the core element further comprising holes or grooves arranged along the longitudinal direction of the arms. The holes or grooves are preferably arranged near the respective edges of the arms. This provides an improved contact between the second element and the core element when the second layer is applied on to the core element In further embodiment of the invention the pulse meter further comprises at least one metal disc being partly embedded in the second layer on at least one of the arms with an exposed metal surface adapted to be in contact with the baby's body in the applied position.

The exposed surface of the metal disc facing inwards from the arm. The results is that the metal surface is in contact with the baby's skin on each side of the body when applied onto the baby. This provides an increased signal quality.

In a further embodiment the at least one metal disc is connected to the first core part at the at least one free end of the arms.

In a yet further embodiment, the pulse meter having two metal discs attached to the respective arms. Both exposed surfaces facing inwards to be in contact with the skin of the baby.

In yet another embodiment of the invention the pulse meter further comprising a third electrode arranged at the underside of the central portion, touching the center of the baby's chest or abdomen. The material of the third electrode could be of metal or made of a conductive polymer. The third electrode provides an improved signal quality of the pulsemeter.

In yet another embodiment of the invention the second layer is in contact with the control unit through a protrusion embedded in an opening in the second layer for transferring the measured signal from the newborn to the control unit.

The pulse meter is preferably configured to be applied around the torso of the baby. The pulse meter is configured to close tightly around the baby's torso in the resting position.

BRIEF DESCRIPTION OF DRAWINGS

FIG. 5a shows a cross sectional view of the pulse meter viewed from below.

FIG. 5b shows a cross sectional view of the core material and the over-molded material in the arms of the pulse meter.

FIG. 6 shows a detail view of the housing with the electronical part of the pulse meter.

FIG. 7 shows the pulse meter viewed from above.

FIG. 8a shows a cross sectional view of the pulse meter with the housing viewed from the side.

FIG. 8b shows a detailed view of the housing from FIG. 8a.

DETAILED DESCRIPTION OF THE INVENTION

Figure 1:
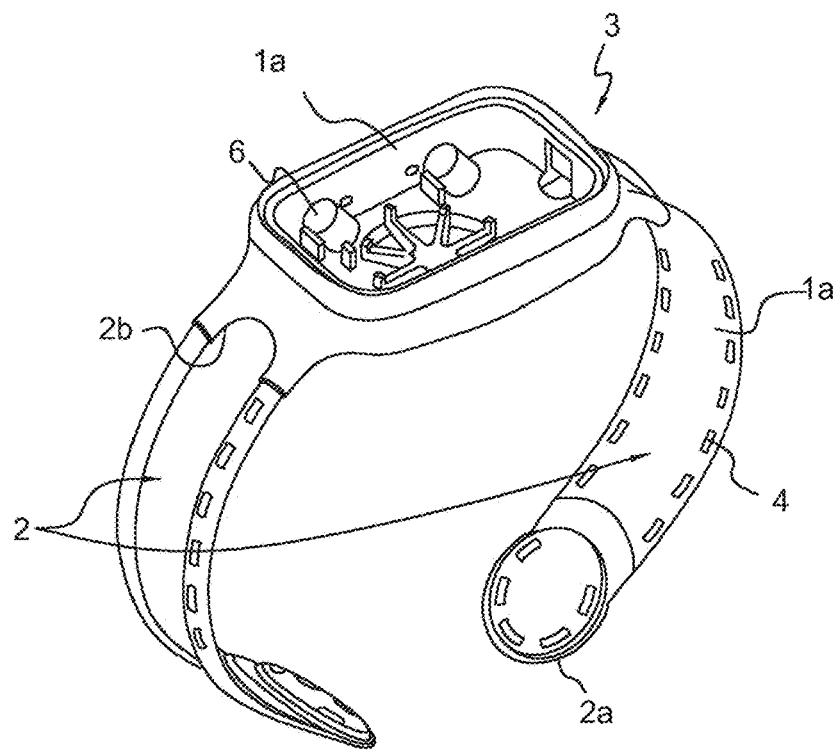
FIG. 1 shows the core element of a pulse meter for a newborn according to the invention.

Having described the main features of the invention above, a more detailed and non-limiting description of non-limiting embodiments of the pulse meter according to the invention.

A pulse meter 1 according to the invention comprises a housing 3 and a control unit 21. The control unit 21 (FIG. 6) is arranged in connection with the housing 3. The housing 3 is also named central portion 3. The pulse meter 1 further comprises two flexible arms 2 extending form the housing 3 at each side of the housing 3. The arms 2 extending from the housing 3 in a bow-shaped manner as shown in the FIGS. 1-4, 8a and 9. The arms 2 having respective a free end 2a arranged in a distal end 2a of the arm 2. as shown in the FIG. 1. The arms 2 and housing 3 are preferably connected in an integrated manner. The arms 2 are thin and flexible with spring back effect that gives sufficient press inward when expanded.

Figure 3:
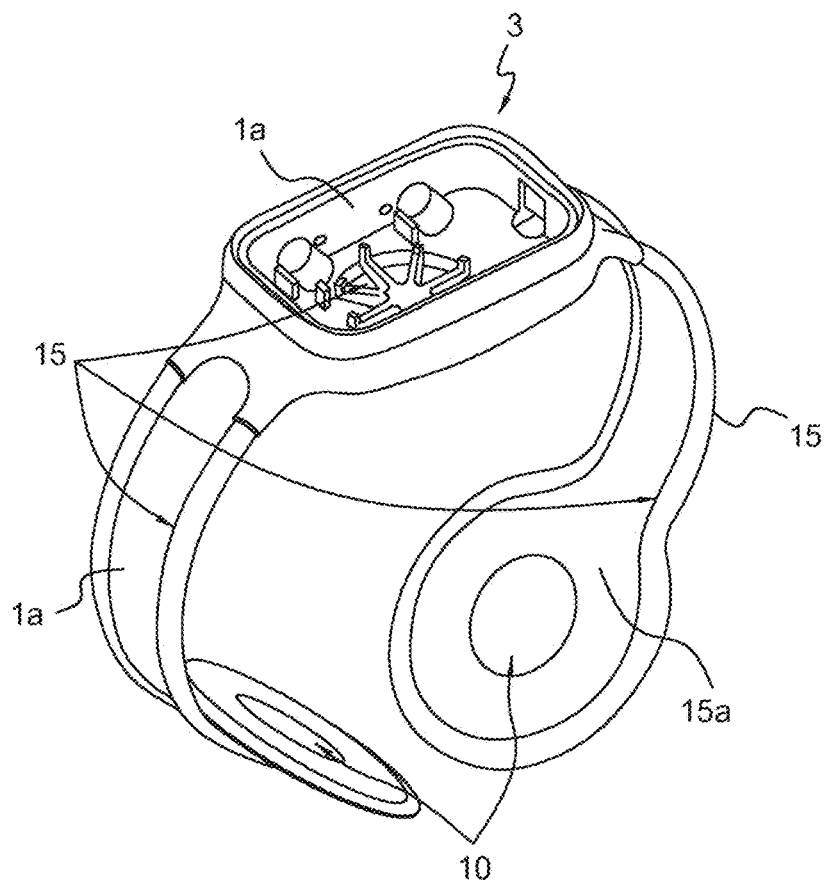
FIG. 3 shows the pulse meter over-molded with an electrically conductive material.
Figure 4:
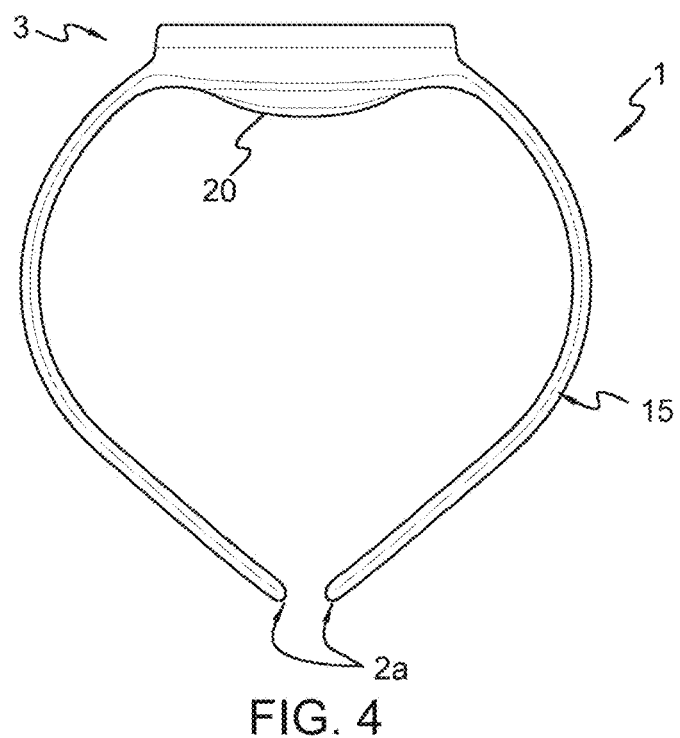
FIG. 4 shows the pulse meter from FIG. 1-3 viewed from the side.

The pulse meter 1 comprises a core element 1a as shown in FIGS. 1 and 3. This core element 1a is made of a material that is hard but highly flexible to allow movement of the arms. This gives the thin, flexible arms 2. The material of the core element 1a has also a spring effect that gives sufficient press inward when expanded.

Possible material of the core element 1a for this purpose could be Polycarbonate (PC), ABS, Polyamide (PA) or POM but also other materials with good spring effect and high break resistance, such as string steel.

Figure 2:
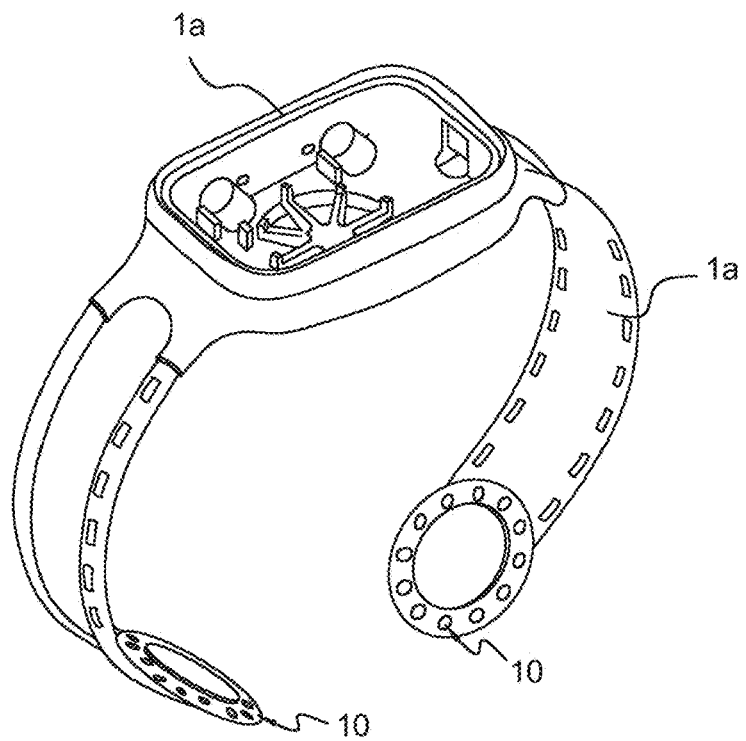
FIG. 2 shows the core element of the pulse meter with metal electrodes.

The core element 1a further comprises "holes" or grooves 4 along the longitudinal edges of both the flexible arms 2 as shown in FIGS. 1 and 2. These holes or grooves 4 provides a better mechanical binding to an overmolded material, which will be shown and described in relation to FIG. 3.

In FIG. 2 there is also shown two metal discs 10 arranged at both the free ends 2a of the flexible arms 2. The metal discs 10 functioning as electrodes to give an optimal contact with the skin. The pulse-meter 1 could however work without the metal disc or electrodes 10. In another embodiment there could also be only one metal disc 10. Without the metal disc or discs 10, it is the surface of a second layer 15 of a material itself that is electrically conductive and that will provide the necessary contact with the skin as will be further described below.

The second layer 15 of the conductive material is covering the inside of the arms 2 and thereby increasing the skin contact area in addition to serve as the electrically conductive body conducting the signals to the control unit 21.

FIG. 3 shows the pulse meter 1 where the core element 1a is over-molded by the second layer 15. This material of the second layer 15 is both soft and electrical conductive. The material could preferably be a polymer. To give the sufficient electrical conductivity along with the required softness and biocompatibility, several polymers may be used.

A suitable overmolded material to be used in the second layer 15 could for instance be carbon filled thermo-plastic urethane (TPU) or other soft material like thermoplastic elastomer (TPE)s, PVC, rubber, silicone etc that contains an electrically conductive additive.

By overmolding the core element 1a with an electrically conductive second layer 15 instead of traditional cables, the pulse-meter 1 is simpler since it provides a production that do not require additional assembly and cable connections. This also results in that the flexible arms 2 could be kept thin since there are no need for a hollow design to embed a cable between the electrodes and the control unit 21.

The reduction of the arm stiffness by avoiding a double layer design to embed a cable-based assembly also provides a product having a surface that is smooth and easy to clean. This is an important feature in a medical device like this.

Another way of obtaining this effect of reduced arm stiffness along with electrical conductivity is to mold or in other ways attach a thin metal sheet to the polymer. Another possibility is to metallize the polymer. The metallizing process is obtained by applying a thin metal coating directly onto the surface of the polymer. These are all possible embodiments of the second layer 15.

Additionally, the second layer 15 create a soft touch around edges 2b that are arranged along each longitudinal side of the arms 2 to give a gentle touch against the baby's body. This provides a soft, well-rounded product.

The metal discs 10 disclosed in FIG. 2 are partly molded by the second layer 15 in the embodiments of the invention that have metal discs 10. This is illustrated in FIG. 3.

A part of the metal disc or electrode 10 are not covered by the second layer 15 to leave an open surface 10a for the metal disc 10.

The exposed metal surface 10a is facing inwards. This provides an optimized contact with the skin for this embodiment and an improved signal quality as mentioned also above.

The second layer 15, forms the inner surface touching the baby's skin. The second layer is also applied around the edges 2b of the pulse meter 1 as shown in the FIG. 5b.

The inside of the flexible arms 2 have a large area made of the second layer 15. This provides a maximum skin contact area and thus maximum heart-signal detection for the pulse meter of both arms 2.

The housing 3 and the surface of the outer side of the pulse meter 1 are not completely covered with the second layer or overmolded material 15. This is illustrated in FIGS. 5a and 5b. In these figures, a cross sectional view through the arm in the transverse direction, showing how the second layer 15 is overmolding the core element 1a at the inner surface of the arms 2 and around the edges 2b. The figures shows further that the core element 1a is not covered by the second layer at the outer surface.

A third electrode 20 could be placed between the two arms 2. The electrode 20 is placed at the underside of the housing as shown in the FIG. 4. The third electrode 20 is adapted to touch the centerline of the baby's torso. In the embodiment shown in FIG. 4, the electrode is situated between the core element 1a and the second layer 15. The third electrode 20 could also be made from the material of the second layer 15.

FIGS. 5a and 5b shows the different layers of the pulse meter 1 in greater detail. These figures illustrates that the core element 1a of the pulse meter 1 is arranged on the outer surface facing away from the baby's torso when in use. The second layer 15 is attached to the inner surface of the core element 1a and extending over the edges 2b at both side of the respective arms 2.

The core element 1a is made of a hard and flexible material while the second layer 15 is made of soft, electrically conductive material, such as a polymer.

FIG. 6-8b shows details of the housing 3 of the pulse-meter 1. The housing 3 comprising the control unit 21. This provides measurement for the heart rates and provides feedback on heart rate via the build in display of the control unit 21. The display 21 could be a PCA with led matrix or any other type of display like for example LCD or O-LED.

The pulse meter 1 could also include a communication device for transferring heart rate data to an external device using for instance bluetooth communication or other wireless transmissions.

The pulse meter 1 could also include an accelerometer that detects the patients position, and that also detects motion. Periods of excessive motion (like during drying or physical stimulation of the newborn) may have a noisy heart rate signal, and the motion detection can help filtering out these periods. The accelerometer can also be used for battery power conservation with introduction of "sleep mode" when the device e.g. is resting on a table, and "wake up" with detection of motion.

The pulse meter 1 could also have rechargeable battery which can be charged on a charging stand by for instance charging pins, inductive charging or by other methods.

Both the communication device and power supply devices could be arranged in the housing 3.

The charging could be powered by an AC power supply that is connected to mains 110-240 V which are known per se.

FIG. 8b shows a detailed view of the how the control unit 21 is connected to the electrically conductive polymer or second layer 15. Its shows that connector pin 22 of the control unit 21 are mated into small openings 23 in the overmolded material 15. The openings 23 corresponds to the protrusions 22. There is thus no need for soldering or crimping to maintain the control unit 21 in contact with the second layer 15. The FIG. 8b show a detail view of one side of the control unit 21 arranged in the pulse meter 1. Both sides of the control unit 21 have the same connection with the connection pin 22 in contact with the second layer 15.

Figure 9:
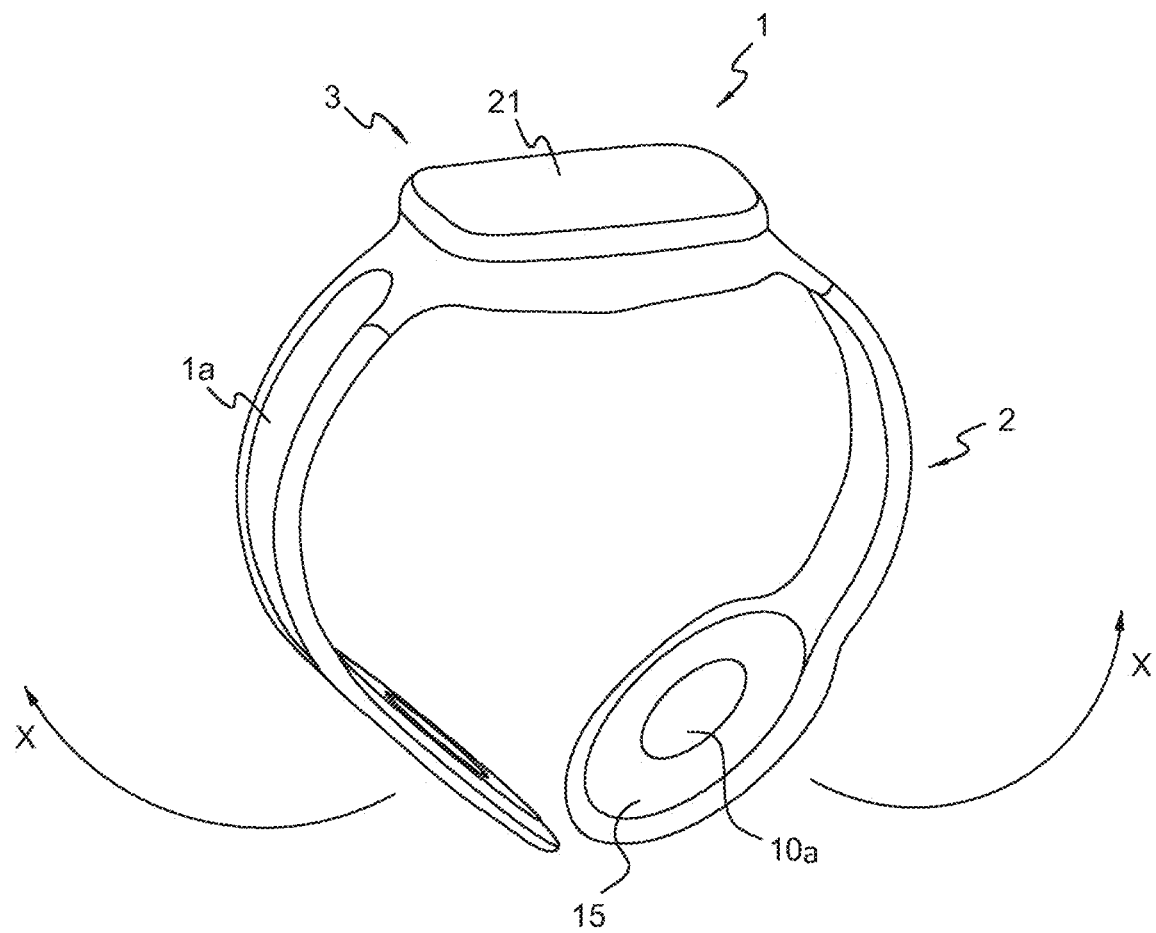
FIG. 9 shows the pulse meter illustrating the spring back effect of the arms of the pulse meter.

FIG. 9 further illustrates the flexibility and the spring back effect of the pulse meter 1.

The arms 2 are adapted to move outwardly away from each other in the direction of the arrows 2 in order to place the pulse meter 1 on the baby's body or torso. The arms 2 will retract in the opposite direction of the arrows X and press against the baby's torso when the pulse meter 1 is placed at the right position on the baby's torso.

The functioning of the pulse meter 1 will be described further below:

The pulse-meter 1 is a medical device for measuring the heart rate of a newborn (within hours after birth). It could preferably be battery powered. By providing heart rate quickly and reliably, it can help assess the need for resuscitation immediately after birth and help guide efforts if resuscitation is needed. The pulse-meter 1 according to the invention is intended to be placed across the torso of the patient (not shown) and will be in contact with the skin.

The flexible arms 2 will thus surround the torso and hold the pulse meter 1 firmly in place during the resuscitation. The electrodes are then in continuous contact with the baby's skin. The pulse meter 1 could be placed anywhere on on the baby's body, but preferably to be arranged in the stomach area where it does not hinder the visibility of the baby's chest.

When not in use, the pulse-meter 1 according to the invention could hang on a charger stand compatible with the pulse meter 1 ready to use or may be powered in another way. The pulse meter 1 could have no buttons and be turned on and off automatically. The pulse meter 1 could also sense when the pulse meter is in contact with a patient. The heart rate will then display in the control unit 21 on a display on top of the pulse meter 1. The control unit 21 will also indicate when the heart rate cannot be calculated e.g. to excessive motion. The pulse-meter 1 can also transfer the heart rate measurement to an external device (not shown), for instance wirelessly using Bluetooth. The pulse meter 1 is also reusable and can be disinfected easily.

The operating principle of the monitor/control unit 21 is to use dry electrodes across the torso from which an ECG based signal is detected and analyzed in the software and from which the calculated heart rate is presented on a display of the control unit 21. The monitor/control unit 21 could for instance be battery powered.

The pulse meter 1 having preferable two different size versions: A pulse meter suitable for newborns of 1.5-5 kg and a smaller version suitable for newborns of 0.8-2.0 kg.

The intended use for the pulse meter 1 according to the invention could be for measurement of the heart rate after delivery of a newborn, in particular during resuscitation. The pulse meter 1 is preferably used by healthcare professionals who have been trained in newborn resuscitation.

A suitable environment for the pulse meter 1 is in hospital environments e.g. delivery room, resuscitation room, and/or operating theatre. Other emergency situation outside of the hospital environments where babies are born/resuscitated (e.g. road ambulances) is also suitable environment for use of the pulse meter 1.

When the arms 2 are expanded to fold around a newborn's torso, the spring effect of the core element 1a together with the overmolded layer 15 causes the product to fold snuggly around the baby's body or torso ensuring a firm grip and electrical contact to the skin. The holding force exerted onto the baby's body is equivalent to the force a trained physician would use to press a stethoscope against the body during auscultation.

To further improve the ECG signal-quality, the third electrode 20 is placed between the two arms 2, touching the centerline of the baby's torso. In this embodiment, as previously described in relation to FIG. 4 this electrode could be molded onto the base structure using the second layer material 15 or a metal.

To conduct the electrical signal from the patient's heart activity (ECG) from the surface of the skin to the electronic control unit 21 in the pulse meter 1, the preferred embodiment uses the second layer 15 which preferably is an electrically conductive polymer. The polymer is at the same time soft and highly flexible to allow for the free movement of the arms 2 and also increase the softness and usability on when in use on the baby's bare skin.

The present invention has been described with reference to preferred embodiments and aspects thereof and related to the accompanying drawings for the sake of understanding only and it should be obvious to persons skilled in the art that the present invention includes all legitimate modifications within the ambit of what has been described hereinbefore and claimed in the attached claims.

The invention claimed is:

1. A pulse meter comprising:
a control unit arranged in a central portion of the pulse meter;
a first arm with an integrated first electrode; and
a second arm with an integrated second electrode;
wherein the first arm and the second arm extend respectively in a bow from opposite sides of the central portion;
wherein the first and second integrated electrodes are configured to be in contact with a body of a new-born patient when in use, the first and second integrated electrodes being electrically connected to the control unit;
wherein the first and second arm and the control unit comprise an integral core element made of a material having flexible properties to allow the first arm and the second arm to bend away from each other when the pulse meter is being applied to or removed from the body,
wherein the material has spring back properties so that the first and second arms naturally contract inwards such that the first and second integrated electrodes are maintained in contact with the body when the pulse meter is in an applied position;
a second layer overmolding at least a portion of each of the first arm and the second arm, the material of the second layer being electro-conductive and forming an electrical connection between each of the first and second integrated electrodes and the control unit; and
wherein the second layer overmolds edges extending along longitudinal sides of each of the first and second arms.

2. The pulse meter according to claim 1, wherein the integral core element is made of a material that is highly flexible and has a resting position adapted to close tightly around the body.

3. The pulse meter according to claim 2, wherein the integral core element consists of a flexible material with good spring back effect.

4. The pulse meter according to claim 3, wherein the flexible material is selected from the group consisting of Polycarbonate (PC), ABS, Polyamide (PA), POM, and spring steel.

5. The pulse meter according to claim 1, wherein the second layer consists of a soft polymer material.

6. The pulse meter according to claim 5, wherein the soft polymer material is selected from the group consisting of carbon filled thermoplastic polyurethane, thermoplastic urethane (TPU), thermoplastic elastomer (TPE), rubber, silicone, and polyvinylchloride (PVC) having an electrically conductive additive.

7. The pulse meter according to claim 1, wherein the material of the second layer is a flexible material.

8. The pulse meter according to claim 1, wherein the integral core element comprises at least one of holes and grooves arranged along a longitudinal direction of the first and second arms.

9. The pulse meter according to claim 1, comprising:
at least one metal disc arranged on at least one of the arms;
wherein the at least one metal disc is partially embedded in the second layer with an exposed metal surface adapted to be in contact with the body in the applied position so that a part of the at least one metal disc is in contact with the body to increase signal quality.

10. The pulse meter according to claim 1, comprising:
two metal discs; and
wherein one of the two metal discs is attached to the first arm and a second of the two metal discs is attached to the second arm.

11. The pulse meter according to claim 1, comprising:
a third electrode arranged at an underside of the central portion; and
wherein the electrode is adapted to be in contact with the body at a point in the center between arms of the body.

12. The pulse meter according to claim 11, wherein the third electrode comprises a conductive polymer or a metal material.

13. The pulse meter according to claim 12, wherein the conductive polymer is the material of the second layer.

14. The pulse meter according to claim 1, wherein the second layer is in contact with the control unit through a connector pin embedded in an opening in the second layer for transferring a measured signal from the body to the control unit.

15. The pulse meter according to claim 1, wherein the arms of the pulse meter are configured to close tightly around a torso of the body.

* * * * *